US008053245B1

(12) United States Patent
Karavolos

(10) Patent No.: US 8,053,245 B1
(45) Date of Patent: Nov. 8, 2011

(54) SYSTEM AND METHOD FOR DETECTING BIOCHEMICALS USING HYDRATED SUBSTRATES BASED ON LIQUID CRYSTAL POLYMERS

(75) Inventor: Angelo Karavolos, Crestview, FL (US)

(73) Assignee: Nanotel Biotechnologies, Inc., Crestview, FL (US)

( * ) Notice: Subject to any disclaimer, the term of this patent is extended or adjusted under 35 U.S.C. 154(b) by 159 days.

(21) Appl. No.: 12/622,258

(22) Filed: Nov. 19, 2009

Related U.S. Application Data

(63) Continuation-in-part of application No. 10/901,895, filed on Jul. 29, 2004, now abandoned.

(60) Provisional application No. 60/490,816, filed on Jul. 29, 2003.

(51) Int. Cl.
*G01N 27/00* (2006.01)

(52) U.S. Cl. ........ 436/149; 436/150; 436/151; 436/532; 422/420; 422/425

(58) Field of Classification Search .................. None
See application file for complete search history.

(56) References Cited

U.S. PATENT DOCUMENTS

| | | | |
|---|---|---|---|
| 4,054,646 A | 10/1977 | Giaever | |
| 4,219,335 A | 8/1980 | Ebersole | |
| 4,394,498 A * | 7/1983 | Kastelic | 528/193 |
| 4,444,892 A | 4/1984 | Malmros | |
| 4,777,019 A | 10/1988 | Dandekar | |
| 4,822,566 A | 4/1989 | Newnan | |
| 6,037,597 A | 3/2000 | Karavolos | |
| 6,064,007 A | 5/2000 | Bernstein et al. | |
| 6,174,405 B1 | 1/2001 | Clarke | |
| 6,179,818 B1 | 1/2001 | Kydonieus et al. | |
| 6,475,728 B1 | 11/2002 | Martin et al. | |
| 6,592,820 B1 | 7/2003 | Hardman et al. | |
| 7,186,567 B1 * | 3/2007 | Sutherland et al. | 436/532 |
| 2005/0079486 A1 * | 4/2005 | Abbott et al. | 435/5 |

FOREIGN PATENT DOCUMENTS

| | | |
|---|---|---|
| EP | 0470650 A2 | 4/1989 |
| JP | 11-293132 | 10/1999 |
| WO | 9857157 | 12/1998 |

OTHER PUBLICATIONS

Iqbal et al. in "High-performance composites based on all-aromatic liquid crystal thermosets", Composites Sceince and Technology, 2011 v. 71, pp. 863-867.*

(Continued)

*Primary Examiner* — Yelena G Gakh

(74) *Attorney, Agent, or Firm* — Lanier Ford Shaver & Payne, P.C.; Jon E. Holland

(57) ABSTRACT

A system for detecting biomaterials that are suspected to be present in a medium that contains multiple materials. A hydrated substrate has water molecules entrapped within molecular spaces between polymeric chains of the substrate. The hydrated substrate also has detection material, which has a specific affinity for a target material. The entrapped water molecules provide a source of water for the detection material such that a change in charge occurs when the target material and detection material coalesce. A display unit detects the change in charge and provides an indication that the target material is present when the change in charge is detected.

16 Claims, 15 Drawing Sheets

OTHER PUBLICATIONS

Karavolos, U.S. Appl. No. 10/901,895, entitled, "System and Method for Detecting Biochemicals Using Detection Material Bonded to Hydrated Substrate," filed Jul. 29, 2004.

Professor Anthony P. F. Turner, "Biosensors: Past, Present and Future," (Cranford University 1996).

Vaidya, Srivathsa, "Clathrates—An Exploration of the Chemistry of Caged Compounds," Resonance, pp. 18-31, Jul. 2004.

Perez, et al., "Cyclopalladated complexes derivates of penylhydrazones and their use as catalysts in ethylene polymerization," Instituto de Quimica, Universidad Nacional Autonoma de Mexico, D.F. Mexico, pp. 291-295, Feb. 15, 2005.

Suslick, et al., "The material chemistry of porphyrins and metalloporphyrins," School of Chemical Sciences, University of Illinois at Urbana-Champaign, pp. 407-413, (2000).

Tabib-Azar, et al. "Fiber optic electric field sensors using polymer-dispersed liquid crystal coatings and evanescent field interactions," Sensors and Actuators, 2000, v. 84, pp. 134-139.

Gotra, et al. (Proceedings of SPIE, 2000) disclose "fiber-optic sensors on the bases of liquid crystals," Proceedings of SPIE, 2000, v. 4239, pp. 76-81.

Brake, et al. (Langmuir, 2002) disclose "an experimental system for imaging the reversible absorption of amphiphiles at aqueous-liquid crystal interfaces," Langmuir, 2002, v. 18, pp. 6101-6109.

Brake, et al. (Science 2003) disclose "biomolecular interactions at phospholipid-decorated surfaces of liquid crystals," Science, 2003, v. 302, pp. 2094-2097.

Every, et al., "Ordered Structures in Proton Conducting Membranes from Supramolecular Liquid Crystal Polymers" J. Phys. Chem. B 2006, 110, 23729-23735.

\* cited by examiner

SYSTEM AND METHOD FOR DETECTING BIOCHEMICALS USING HYDRATED SUBSTRATES BASED ON LIQUID CRYSTAL POLYMERS

CROSS-REFERENCE TO RELATED APPLICATIONS

This application is a continuation-in-part of and claims priority to U.S. patent application Ser. No. 10/901,895, entitled "System and Method for Detecting Biochemicals Using Detection Material Bonded to Hydrated Substrate," and filed on Jul. 29, 2004, which is incorporated herein by reference. U.S. patent application Ser. No. 10/901,895 claims priority to U.S. Provisional Application No. 60/490,816, entitled "System and Method for Detecting Biochemicals using Detection Material Bonded to Hydrated Substrate," and filed on Jul. 29, 2003, which is incorporated herein by reference.

FIELD OF THE INVENTION

The present invention generally relates to the field of sensor technology and, in particular, to systems and methods for detecting a target material that reacts with detection material bonded or otherwise coupled to a hydrated substrate.

RELATED ART

Sensors are used in a variety of applications such as chemical manufacturing processes, petroleum processes, biomaterial detection, hazardous material detection, identification of explosive ordinances, or toxic materials in packages at mail or materials centers. Sensor development continues to improve as material science, chemistry, biochemistry and engineering technology make advances. To address concerns related to terrorist threats and military actions, it is desirable to have portable detection equipment with multiple sensing capabilities. As advances are made in the medical arts and sciences, there is also a need for sensors that will detect and quantify antigens, anti-bodies, enzymes etc. It is desirable that such sensors be small, accurate, and have multiple detection capabilities. Sensors utilized in chemical and petroleum processes have requirements similar to those for defense and medicine.

In general, biomaterial sensors are devices that use a detection material with characteristics suitable for a detectable reaction with a specific biochemical, where the biochemical is designated as a target material. For example, an anti-body, capable of providing a defense against a specific invading antigen, could serve as a detection material for the antigen, the target material. There are tables contained in biochemistry handbooks that provide information on target-detection material complementary pairs. However, it would understood by those skilled in the art that no list is comprehensive since new viruses, bacteria, hazardous materials, synthesized biomaterials and other materials are continuously evolving and being developed. The combination of improvements in micro-processing and science provides opportunities for the development of novel sensors.

The basic principle utilized by sensors is that when a specific detection chemical and a target material react, the reaction produces a chemical reaction, physical reaction, magnetic or electric response at the site of the detection material and/or affects the physical properties of the detection material. By quantifying changes in the properties of a detection material, it is possible to detect the presence and perhaps the quantity of a target material.

BRIEF DESCRIPTION OF THE DRAWINGS

The invention can be better understood with reference to the following drawings. The elements of the drawings are not necessarily to scale relative to each other, emphasis instead being placed upon clearly illustrating the principles of the invention. Furthermore, like reference numerals designate corresponding parts throughout the several views.

DETAILED DESCRIPTION

The present invention generally pertains to systems and methods for detecting target material suspected of being present in a liquid, gas or solid medium. In a preferred embodiment of the present invention, a detection material (selected for properties associated with the target material) is deposited and bonded to an area of a substrate capable of receiving and holding water molecules. When the target material reacts with the detection material, the physical characteristics of the area change. One such detectable change may be a change in the electrical charge of the area. A detection plate, such as a charge couple device (CCD), detects the change in charge and sends a detection signal to electrical processing circuits that preferably amplify and filter the signal and then forward a processed signal to a display device. The display device preferably is a visual device such as a meter, video display or LED that indicates the presence of target material. If the detection system is calibrated, it not only may indicate the presence of a target material, but it also may indicate the quantity of the target material.

It may be useful to provide a general description traditional sensor technology. If a sensor is used to detect a selected target material, such as a hazardous gas, it is generally necessary for the sensor to comprise a detection material that detects that specific selected target material. Target materials are typically detected by a detection material that has a specific affinity for the target material. Target materials and detection materials may be described as a reactive pair. When a target material and a detection material react, changes in the physical properties of the detection material are detectable. The changes in the physical properties may be observed by detecting a change in charge, by detecting a change in response to electromagnetic radiation which includes light of various wavelengths, or by some other well known techniques. In general, charge detectors look for a change in voltage or current, and optical detectors look for a change in optical characteristics resulting from the reaction of the target material and the detection material.

For some sensors, it may be necessary to identify or synthesize a detection material for a specific target material if none is known or is readily available. Furthermore, it is important to note that some detection materials require a specific environment for the detection materials to maintain their structural integrity and sensing ability. For example, some detection materials may breakdown if the temperature gets too high, while other detection materials must be in contact with a liquid, such as water, in order to maintain their sensing properties.

Figure 1:
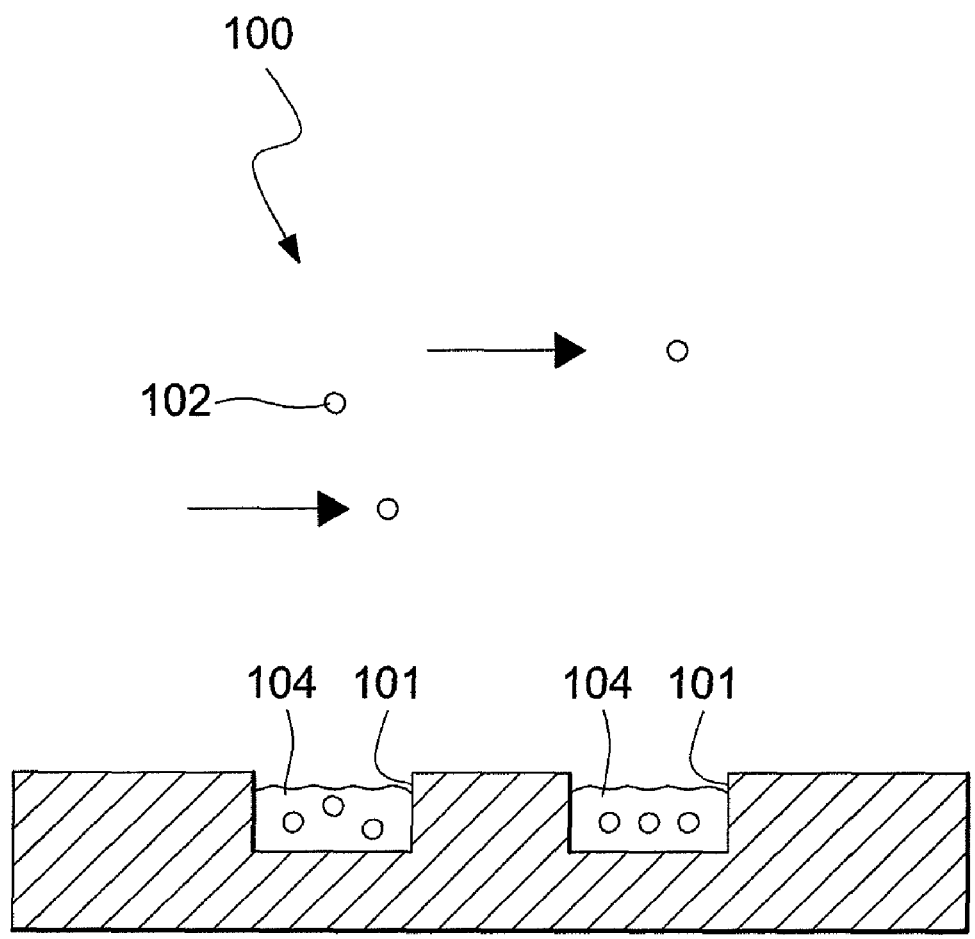
FIG. 1 is a diagram illustrating a prior art substrate for holding detection materials in an aqueous solution.

FIG. 1 depicts a prior art sensing system 100 having a substrate with wells (openings or cavities) 101 for holding a detection material 104 that requires a liquid for maintaining its physical and chemical viability. When a medium containing molecules of a target material 102 passes over the wells of the detection system 100, some of the target material reacts with the detection material 104. The physical properties of the detection material within the well 101 changes, and such changes are observable by a detection device (not shown). The detection device indicates the presence of target material (typically when it exceeds a threshold level), and may also indicate the concentration level of the target material 102 within the medium passing over the wells of the detection system 100.

As stated above, it is known that, certain detection materials such as biomaterials, enzymes and other materials must be immersed in or otherwise in contact with a liquid in order that the detection materials maintain their chemical and physical viability and therefore their detection abilities. The prior art system 100 of FIG. 1 contains liquid within wells 101 and must be oriented in a non-spill position, e.g., the opening of the wells must face upward, to avoid the loss of the liquid containing the detection material 104. Such a position requirement is a disadvantage for many applications, such as for a portable detection device, since an unintentional orientation may cause the liquid and detection materials to be partially or entirely spilled from the wells, thereby rendering the detection system non-functional.

Figure 2:
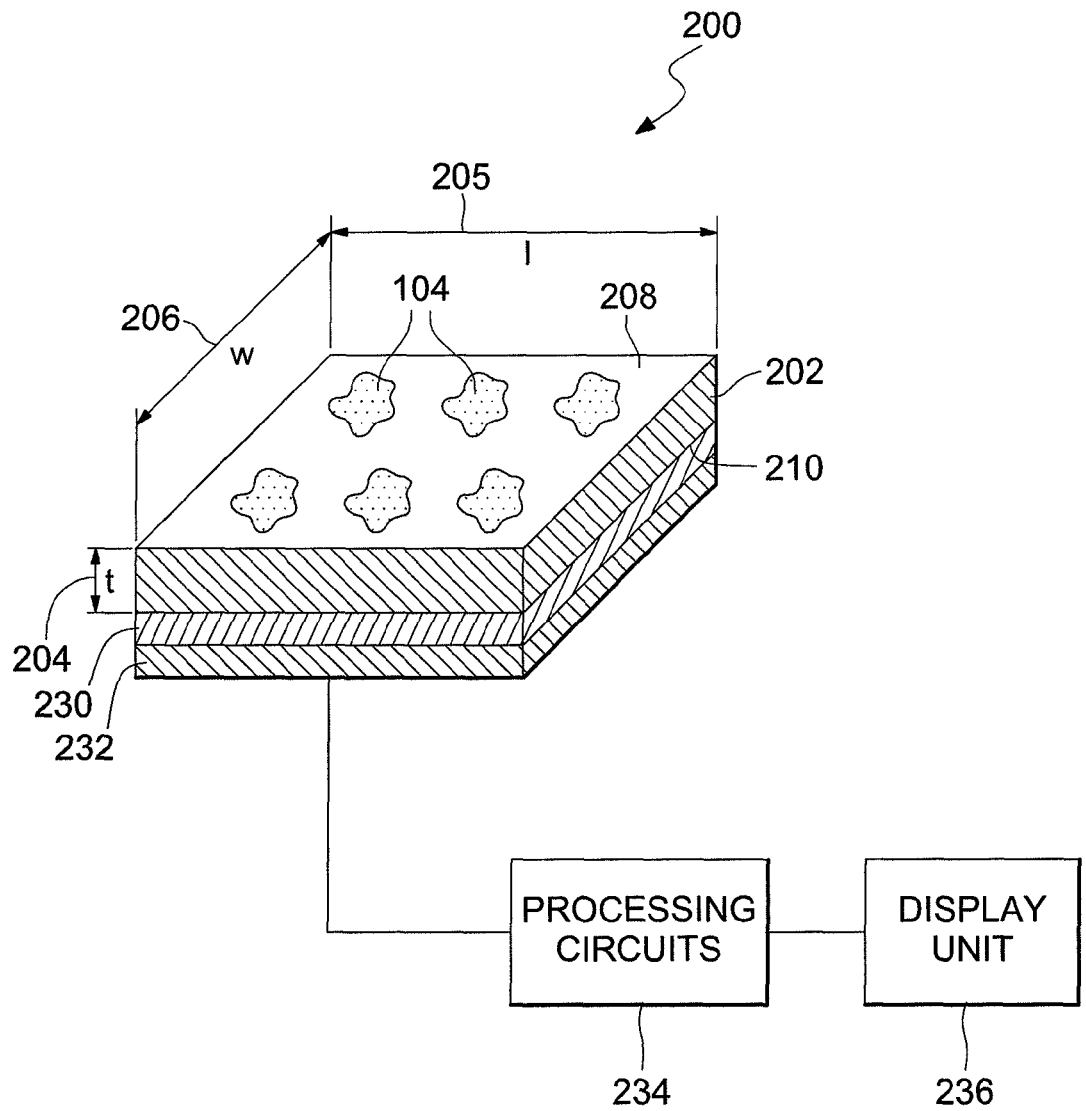
FIG. 2 is a diagram illustrating a detection system using a hydrated substrate that comprises a detection material.

An exemplary embodiment, in accordance with the present invention, of a sensing or detection system 200 for overcoming the limitations of the conventional system of FIG. 1 is depicted in FIG. 2. The system 200 of FIG. 2 comprises a hydrated substrate 202 that may be used to detect at least one target material. A "hydrated substrate" refers to any material that has liquid (e.g., water) molecules entrapped within molecular spaces in the material. In a preferred embodiment, the hydrated substrate 202 comprises a liquid crystal polymer (LCP) that has molecular spaces formed between polymeric chains of molecules. Water molecules are trapped within the molecular spaces, and such water accommodates detection materials that need water to enable detection of the target material. LCP consisting of long polymeric chains, such as benzene rings and other monomers connected by carbon, are capable of confining water between the polymeric chains.

In one exemplary embodiment, small gas bubbles are introduced within polymeric material, which is hydrophobic, thereby leaving voids between polymeric chains. The voids are sized such that water molecules enter the voids when the substrate is immersed in water and such that the water molecules are entrapped within the voids. The selected polymeric material is soluble in organic solvents but not liquid water. Exemplary techniques for forming a hydrated substrate will now be described in more detail below.

In this regard, LCP is softened by immersing it within a solvent, such as benzene, acetone, or naphthalene. While the material is in the softened state, just before it completely dries, metal nano-particles or metal powder is added to the LCP. It is then allowed to dry under atmospheric temperature and pressure. The result is a homogeneous mixture of LCP and metal ions dispersed between cross links of the polymer chains. After a period of about 24 hours, the material is blended using a blender to generate a uniform homogenous powder. The powder is then mixed with polypropylene, polyethylene, and methylated cellulose to increase electrical conductivity, rigidity, and water adsorptivity.

The material is then placed in an extrusion device at a specific temperature, such as about 325 degrees Celsius, for about 30 minutes and drawn through the extrusion chamber at a rate of about 0.1 centimeter per minute, allowing the molecular chains of the polymer to organize into long strands of material. This process is referred to as polymerization.

Gas molecules are introduced into the material while it is still in the melt or glass transition phase. In this regard, during the time when the polymeric strands are just exiting the extrusion chamber, they are introduced to an inlet gas, such as ozone, having negatively charged ions. The gas can be fed through a tube, and the pressure and temperature of the gas can be regulated by an external temperature control gauge and valve to control the size of the gas bubbles that form in the polymeric material. The gas permeates through the polymeric material, and the ions in the gas are attracted to the positively charged metal ions in the polymer strands. Once the fibers cool, the gas is trapped between the polymeric strands leaving molecular pockets in which water molecules may enter and become entrapped when the hardened material is immersed in water. In this regard, during the introduction of gas to the polymeric material, the temperature and pressure of the gas are controlled such that the resulting voids are appropriately sized to receive water molecules with the water molecules becoming entrapped in the voids. That is, after formation of the voids, the polymer has properties that enable the polymer substrate to entrap water molecules within the voids formed by the gas bubbles thereby hydrating the substrate for use as a sensor or other device, as described in more detail herein. By immersing the substrate in water, water molecules migrate into the voids. Subjecting the substrate to a slight pressure increase during immersion helps to increase the migration rate of the water molecules.

The detection material can be added to the substrate in a variety of ways. For example, after blending while the polymeric material is in a powder state, the powder may be mixed with detection material (e.g., a protein or enzyme specific to what is desired to be identified) in a storage container at atmospheric temperature and pressure. The mixture may then be subjected to a mild temperature and pressure increase that does not denature the structure of the detection material. The detection material is driven by pressure and diffusion gradients toward the center of the mixture.

In another example, after formation of the voids, the substrate is immersed in a solution containing water molecules and molecules of the detection material. Some of the molecules of the detection material may be trapped in the voids, particularly if the number and size of the molecules of the detection material are similar to the water molecules.

In addition, quantum clusters of detection material may be anchored into the substrate 202 using an array of pins with nano-clusters of the detection material on the tips. The size of the pins may be selected such that the holes have a diameter from approximately 5 to 15 nanometers, although other diameters are possible. In such case, the molecules of the detection material become entrapped in the holes stamped into the substrate 202. Even if the pins are not so sized, the stamping of holes may improve the ability of the detection device to detect a change in charge since portions of the detection material may be closer to the bottom surface 210.

Figure 15:
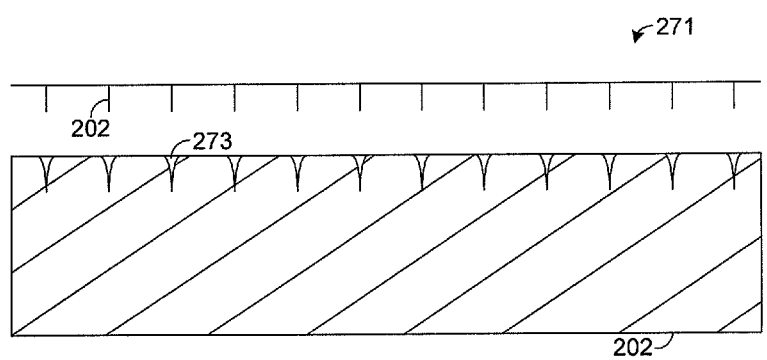
FIG. 15 depicts a cross-sectional view of the substrate of FIG. 14 after a stamp having pins have pin used to form holes in the substrate.
Figure 16:
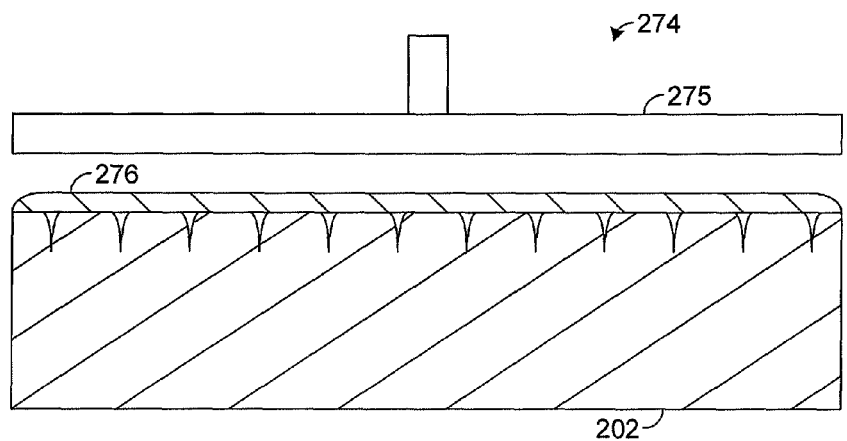
FIG. 16 depicts a cross-sectional view of the substrate of FIG. 15 after detection material has been deposited on the substrate.
Figure 17:
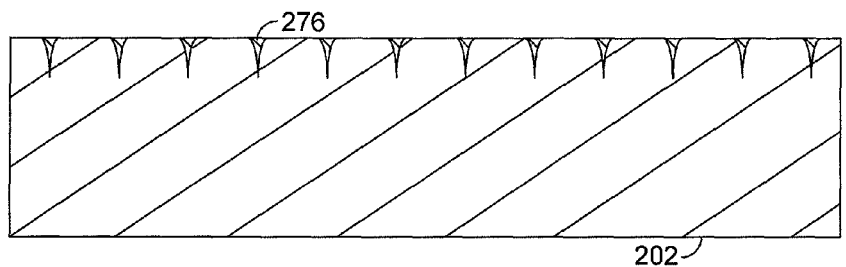
FIG. 17 depicts a cross-sectional view of the substrate of FIG. 16 after a press depicted by FIG. 16 has been used to force detection materials in the holes formed by the pins of FIG. 15.

FIGS. 14-17 illustrate an exemplary method of embedding detection material in a hydrated substrate 202. In this regard, a stamp 271 having a plurality of pins 272 is pressed against the substrate 202 such that the pins 272 puncture the substrate 202 leaving holes 273 in the substrate 202 when the stamp 271 is lifted, as shown by FIG. 15. Referring to FIG. 16, detection material 273 is then deposited or otherwise formed on the substrate 202, and a stamp 274 having a flat plate 275 is pressed against the detection material 276 forcing some of the detection material into the holes 273, as shown by FIG. 17. The excess detection material 276 on the top of the substrate 202 may be removed via any suitable process for removing layers of substrates.

In an exemplary embodiment, depicted in FIG. 2, a hydrated substrate 202 has detection material contained within the substrate 202. Hydrogen ions within the substrate serve as a source of water for the detection material placed in or on the substrate 202.

Still referring to the exemplary embodiment illustrated in FIG. 2, the hydrated substrate 202 may have a variety of dimensions. In one exemplary embodiment, the substrate has a thickness 204 of several microns and has a width 205 and a length 206 less than a centimeter, although other dimensions are possible.

Reaction of the target material 102 and the detection material 104 preferably causes changes in physical properties of the detection material 104. In the present exemplary embodiment, a reaction between the target material 102 and the detection material 104 causes changes in the electrical charge properties of the detection material. However, in other embodiments the reaction may cause other types of physical changes in the detection material 104.

A detection plate 232, such as a metallic plate or a charge coupled device (CCD), is bonded or otherwise coupled to the bottom surface of the substrate 202 via a bonding material 230. This detection plate 232 determines when reactions between target material and detection material have occurred. For a discrete area containing detection material 104, the detection plate 232 preferably is sensitive to and observes changes in charge within the detection material 104, and detection plate 232 therefore detects when such detection material 104 comes into contact with target material 102.

In this regard, the target material 102, suspected of being present, makes contact with the detection material 104 when a medium containing the target material flows over the top surface 208 or otherwise comes in contact with the top surface 208 of the hydrated substrate 202. Such contact causes a reaction between the target material 102 and the detection material 104. This reaction releases electrons causing a voltage change. The detection plate detects this change in voltage thereby detecting the chemical reaction and, therefore, the presence of the target material 102 that is in contact with the detection material 104. Because the detection voltage may be weak, the detection plate couples a detection signal to processing circuits 234. The processing circuits 234 preferably amplify the detection signal, determine if a threshold level has been reached, determine the amount of target material present or provide other processing requirements as desired. A display unit 236 is coupled to the processing circuits 234 for displaying the change of voltage information. The display unit 236 may be a voltmeter, a LED, a sound generator, a video screen or various other information displaying devices known to those skilled in the art.

Figure 3:
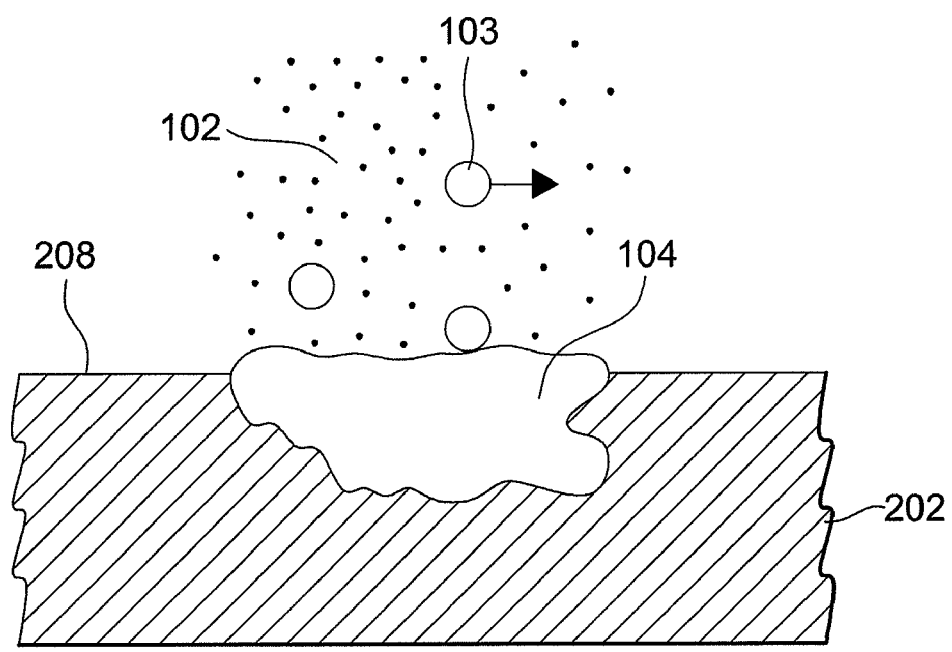
FIG. 3 is a diagram illustrating a reaction of target material with detection material at a location on the hydrated substrate depicted in FIG. 2.

The interaction between the target material 102 and detection material 104 within the hydrated substrate 202 as shown in FIG. 2 is depicted in more detail in FIG. 3. The target material 102 is typically in a medium, such as a liquid or a gas mixture, and is shown above the molecular pocket binding detection material 104 to the hydrated substrate 202. The target material 102 may be in a medium that is moving across the top surface 208 or may be a sample of target material 102 resting upon or otherwise in contact with the detection material 104. When the medium containing the target material 102 contacts the top surface 208 of the substrate 202, some of the target material 102 preferably reacts with the detection material 104 and preferably provides changes in physical properties that are detectable. These changes in the physical properties, within the area containing the detection material 104, are preferably observed by a measurement device. When a change in charge occurs, the detection plate 232 preferably provides a detection signal that is coupled via processing circuits to a display unit. If the conductivity, dielectric constant or optical properties change, techniques are available for detecting and observing such changes. The hydrated substrate 202 containing detection material 104 provides a variety of physical property changes that may be observed. Advantages of the exemplary system 200 over traditional sensors 100 is a smaller size, an improved sensitivity and the ability of the hydrated substrate 202 to maintain the structural integrity of detection materials requiring a liquid such as water.

Figure 4:
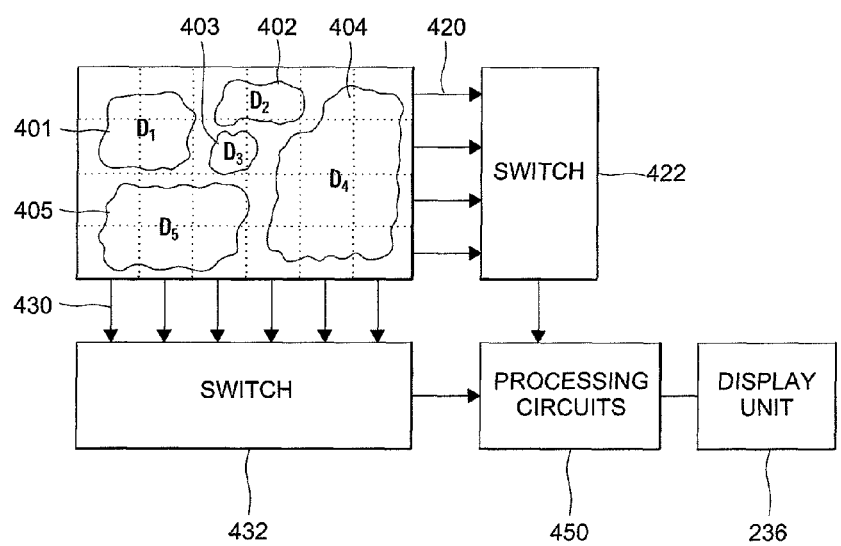
FIG. 4 is a diagram illustrating the bonding of several detection materials to the hydrated substrate similar to the illustration depicted in FIG. 2.

Because the hydrated substrate 202, as described above and discussed in FIG. 2, is thin and can have molecular-sized voids for holding specific detection materials, it is possible to deposit multiple detection materials on defined areas of the hydrated substrate 202 in one exemplary embodiment, as depicted in FIG. 4. When the substrate has multiple detection materials, a single sensor may simultaneously detect multiple targets, as will be seen.

A view of the top surface 208 of the hydrated substrate 202 shows multiple areas 401-405. Each of these illustrated and defined areas 401-405 may have a different size and shape selected in accordance with the requirements of the sensor. For example, if there is a large quantity of a first target material in a medium and the corresponding detection material pair is sensitive to the first material, a small area may be preferable, such as area 403. If there is a small quantity of a second target material, then a large area such as area 404 may be preferable for detecting the second target material. The size of the area selected for a given target material may be dependent on the observation properties of the reaction pair and the quantity of target material 10 in the medium. When these are multiple areas, each having a specific detection material, it may be necessary to modify the processing circuit interface. The detection plate 232 for the sensor system of FIG. 4 preferably is divided into sections and samples related to each identified area 401-405 are sent to processing circuits 450. Switches 422 and 433 may be placed in a grid arrangement and sample detection voltages from each area of the grid arrangement. The processing circuits 450 then amplify and process the sampled detection voltages and send the results to the display unit 236. For a sensor system having multiple detection materials, a graphic display may be preferred, although other types of display may also be used.

Figure 5:
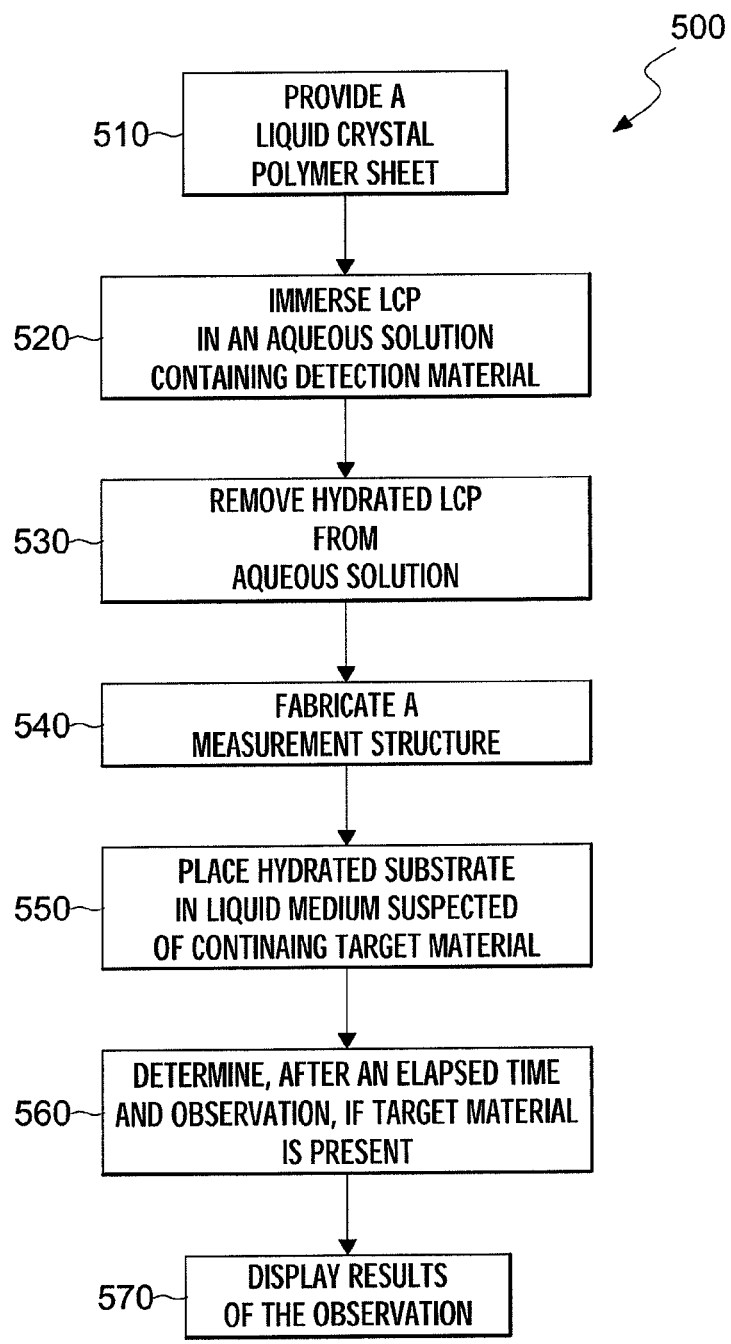
FIG. 5 is a diagram illustrating an exemplary process for making the detection material of FIG. 2.

A first exemplary processing method for fabricating the sensor system 200 of FIG. 2 is depicted in FIG. 5. The process 500 starts with step 510, providing a sheet of LCP having voids appropriately sized to trap water molecules and molecules of the detection material. The LCP is then immersed, step 520, in an aqueous solution having detection material 104. The LCP sheet remains in the solution for a period of time in order for water and detection material molecules to migrate into the molecular pockets of the LCP sheet. Slightly pressurizing the sheet during immersion helps to fill more voids with molecules of water and detection material. Next, the LCP sheet, now hydrated and having detection material 104, is removed 530 from the aqueous solution and excess solution is removed. The excess solution may be removed by some mechanical means such as gravity (hanging the LCP so the liquid will run off), or by the flow of air over the surface that pushes the excess liquid from the LCP sheet. Next, a measurement structure is fabricated 540, such as shown in FIG. 2. An exemplary measurement system may have the detection plate 232 or multiple plates bonded to the bottom surface of the LCP sheet. A CCD may serve as the detection plate 232. Conductors may be connected to the detection plate 232 so that detection signals may be coupled to the processing circuits and to the display unit. The sensor system is then placed, step 550, in a medium suspected of containing target material 102. A medium having the target material 102 may flow over the top surface 208 of the hydrated substrate or a sample or drop of a medium may be placed on the top surface 208 of the substrate 202. After an elapsed time, a detection signal may be observed and a determination 560 of target material presence and/or quantity is then sent to a display unit 236. The display unit then displays information, step 570, to an observer.

Figure 6:
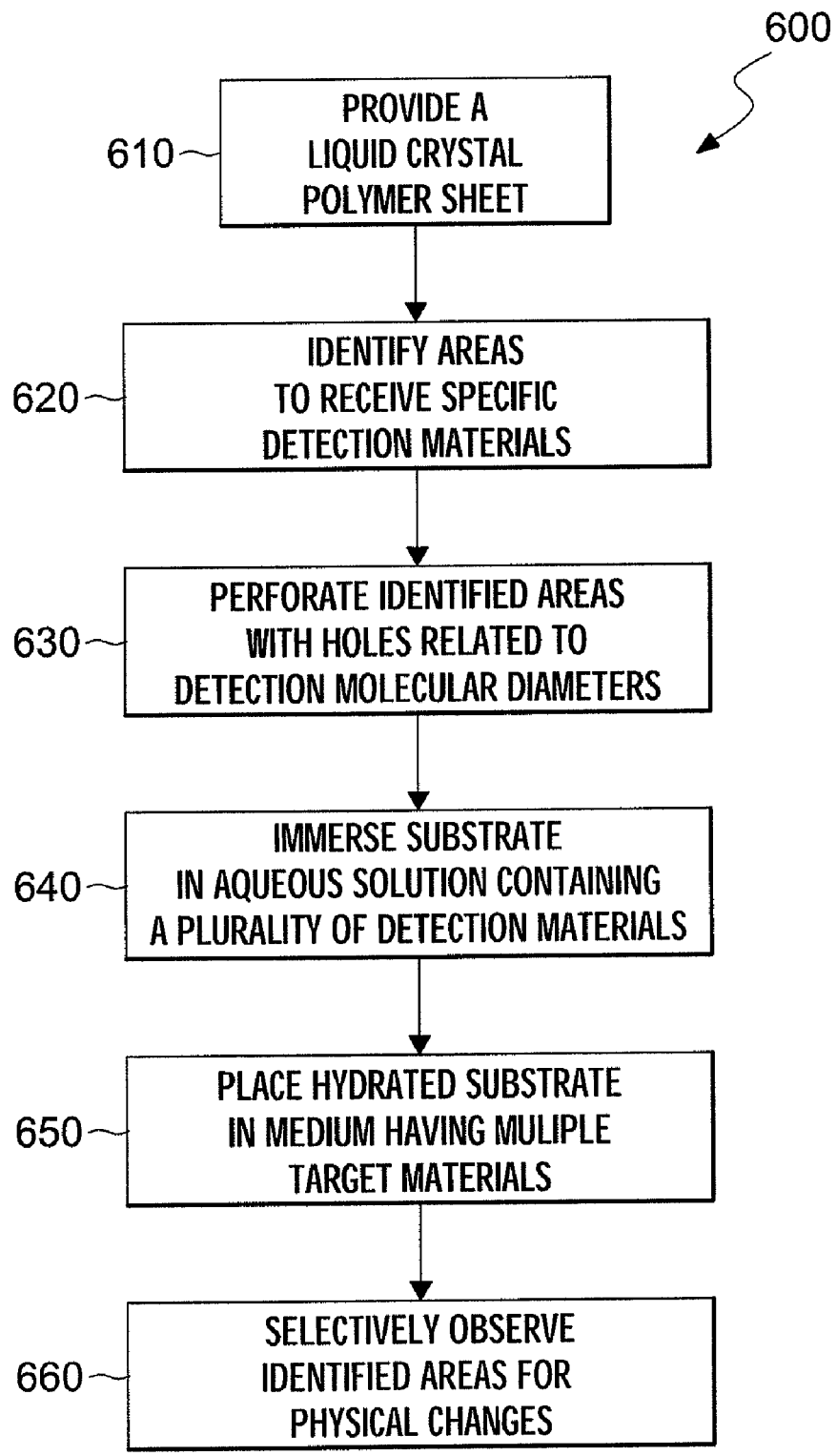
FIG. 6 is a diagram illustrating an exemplary process for manufacturing a detection system with detection materials bonded to several areas of a hydrated substrate as shown in FIG. 4.

FIG. 6 depicts an exemplary process 600 for applying multiple detection materials. First, a LCP sheet is provided, step 610, for a substrate. Next, areas are identified, step 620, for each specific detection material of the multiple detection materials. When the diameter of each of the detection material molecules is known, sized perforations are stamped with pins in the identified areas 401-405, step 630. The sizes of the perforations in the identified area are approximately the size of the molecular diameter of the detection molecules to be inserted in the perforations. The LCP sheet preferably is placed in an aqueous solution containing all the detection materials. Each area receives desired detection material (i.e., the detection material that fits within the area's perforations) via a sedimentation process, step 640. In addition to the sedimentation process, it is possible to sequentially immerse the LCP with perforations in aqueous solutions each containing a single detection material. Next the sensor system, having multiple detectors, is placed in a medium suspected of having multiple target materials, step 650. The identified areas are then observed to determine the presence of multiple target materials, step 660.

Figure 7:
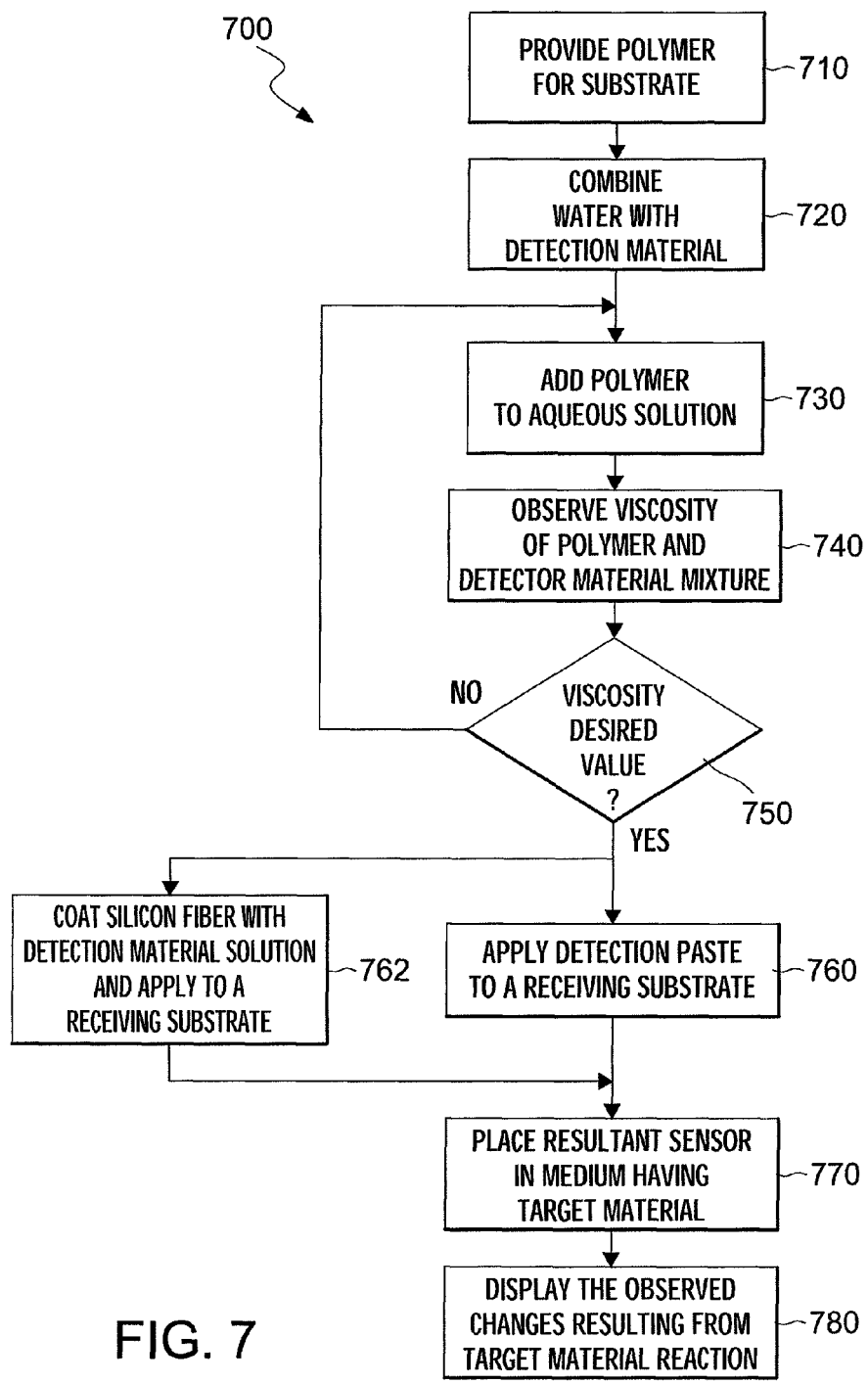
FIG. 7 is a diagram illustrating an exemplary process for making and utilizing the detection material of FIG. 2.

Another exemplary process 700, depicted in FIG. 7, for fabricating the sensor system 200 of FIG. 2 is based on coating a silicon fiber (similar to fiber glass) with detection material 104 and then attaching the coated silicon fiber to a substrate, such as a LCP sheet or a metallic plate. First, a polymer for forming a substrate is provided, step 710. An aqueous solution of detection material is provided for receiving the polymer, step 720. The polymer is added to the aqueous solution containing detection material, step 730. The viscosity of the solution containing the polymer, water and detection material is observed, step 740. The solution preferably becomes viscous as more polymer is added. If the mixture does not have a desired viscosity, the NO path of step 750, more polymer is added. When the desired viscosity is reached, the YES path of step 750, a silicon fiber is immersed in the solution and after a time removed from the mixture, step 762. It may be desirable for the viscosity of the solution to allow the detection material to cover all of the silicon fibers. After detection material covers the silicon fibers, it is preferably annealed to provide bonding. The annealed silicon fiber having detection material 104 may then be pressed onto a receiving substrate. In a variation of the processing method 700, the mixture may have a greater viscosity providing a detection paste. The detection paste is removed and applied 760 to a receiving substrate, such as a LCP. Preferably, the receiving substrate having the detection paste is annealed or dried so that a thin consistent layer of detection material adheres to the receiving substrate. When a LCP is used as the material of the receiving substrate, the process provides a detection element similar to the hydrated substrate 202 of FIG. 2. If the detection paste is applied to receiving substrate such as a metallic plate, the metallic plate may serve as the detection plate 232. The combining of the paste with the receiving substrate provides an element similar to the hydrated substrate 202 with detection material 104 as shown in FIG. 2.

Another exemplary process for inserting and bonding a selected detection material and water (or other liquid) within a LCP requires adding steps to the LCP sheet manufacturing process. First, it is desirable to review the sequence of manufacturing steps for making the LCP sheet and then determining which of the steps may be harmful to a detection material. Any of the no-harm steps not followed by a harmful step, may be modified to include an insertion step for putting an aqueous detection solution in the polymer(s) of the sheet. Although there are a variety of manufacturing processes for making LCP sheets, many of such processes may be suitable for including the insertion step.

Figure 8:
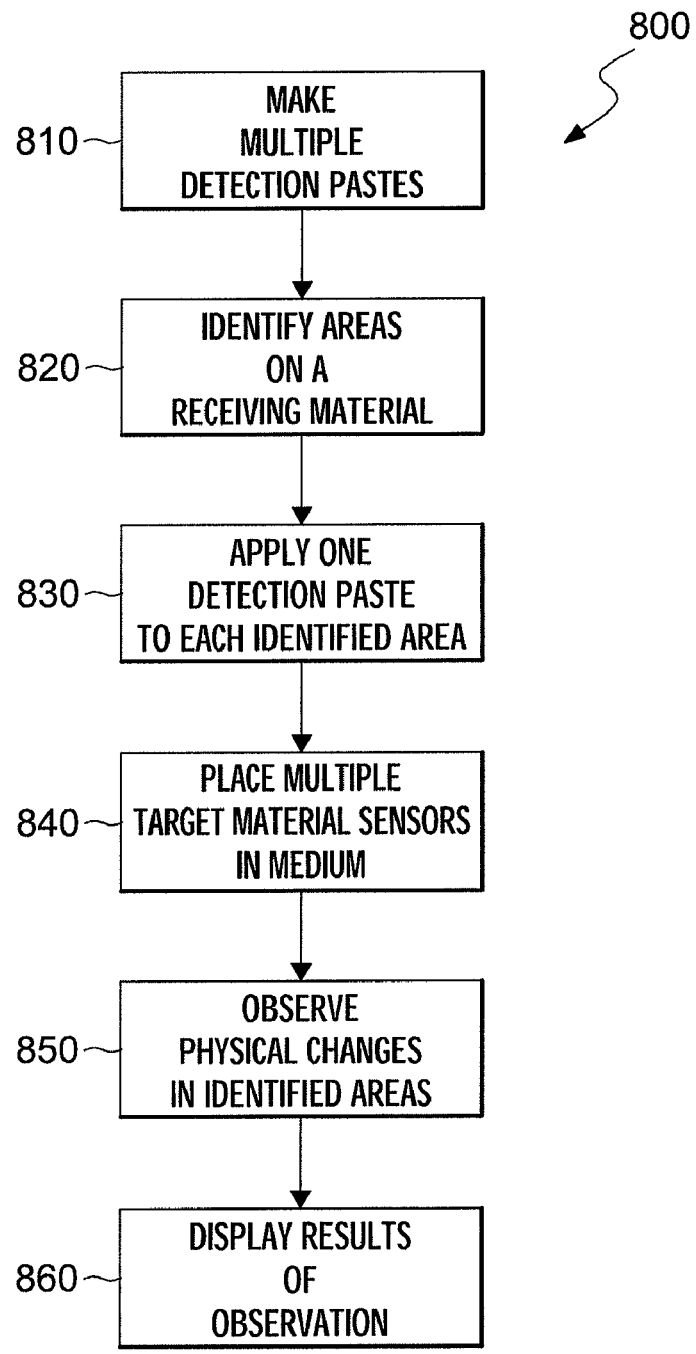
FIG. 8 is a diagram illustrating an exemplary process for manufacturing a detection system with detection materials bonded to several areas of a hydrated substrate as shown in FIG. 4.

A yet another exemplary method 800 for providing a sensor with multiple detection materials, to provide the system of FIG. 4, is illustrated in FIG. 8. The first step is to make multiple detection pastes, step 810, using the process as described in FIG. 7. Each detection paste is selected to react with a specific target material. Areas are then identified, step 820, on a receiving substrate and pastes are applied to the identified areas 830. As a variation in applying the multiple detection materials, multiple silicon fibers, each having a different specific detection material are fabricated. Next, portions of each of the detection material coated silicon fibers are sized and pressed on the receiving substrate. After the multiple detection materials are placed on the receiving substrate and the sensor is placed in a medium having multiple target materials, step 840, observations, step 850, are displayed, step 860, on a display unit 236.

Figure 9:
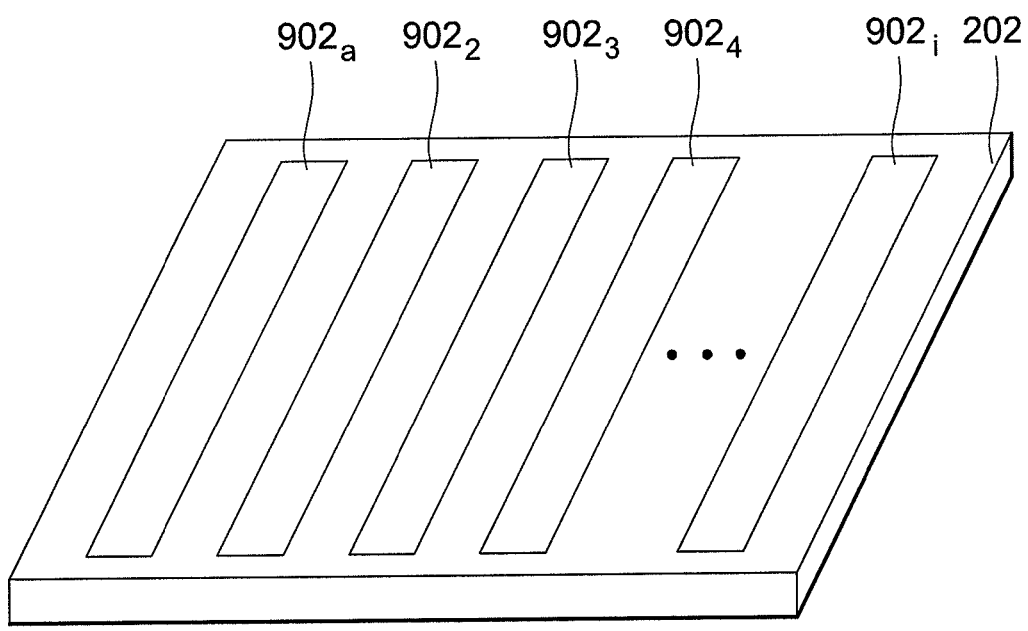
FIG. 9 illustrates an exemplary hydrated substrate having strips of detection material.
Figure 10:
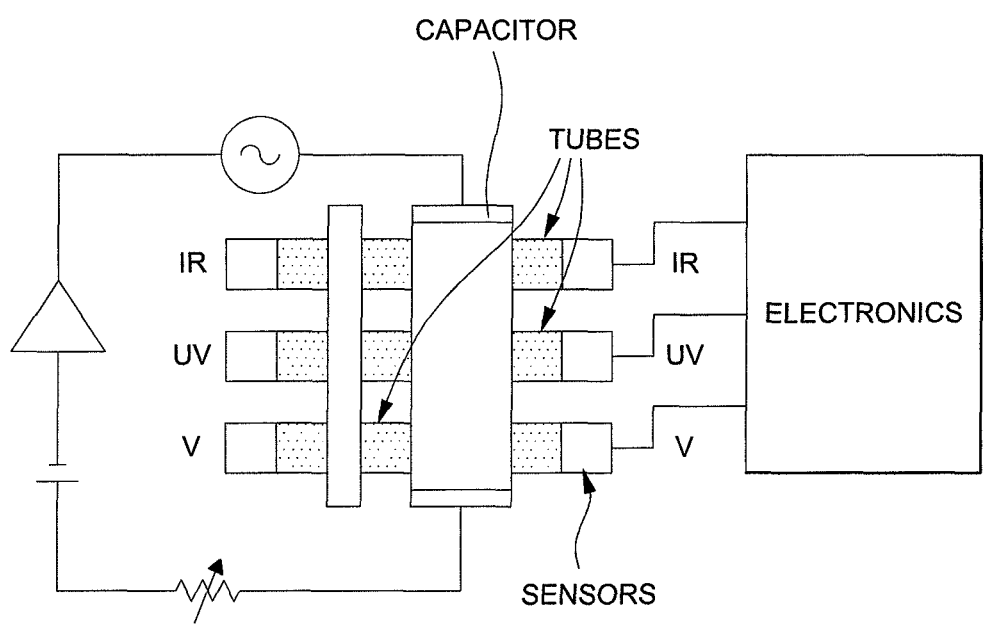
FIG. 10 illustrates an exemplary optical scanning device that was the hydrated substrate of FIG. 9.

Another method of observing changes in the physical changes caused by the reaction of target material 102 and detection material is shown in FIG. 9. The identified areas shown in FIG. 4 are placed in strips as shown in FIG. 9. Each of the strips 902i contains a different detection material 104. In one embodiment the strips, as shown in FIG. 9, preferably have changes in their optical properties when reacting with target materials. By radiating the strips with light of varying wavelengths, in a viewing chamber such as depicted in FIG. 10, such observations may indicate the absence or presence of target material 102.

Figure 11:
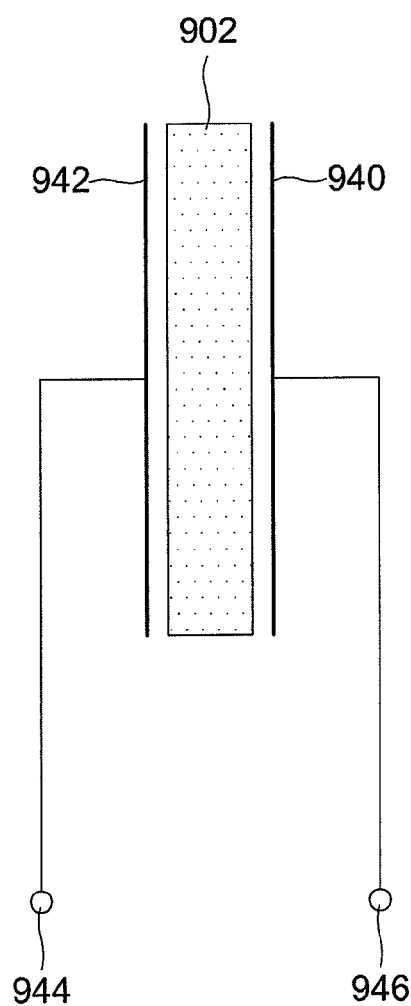
FIG. 11 illustrates an exemplary capacitance device that uses the hydrated substrate of FIG. 9.
Figure 12:
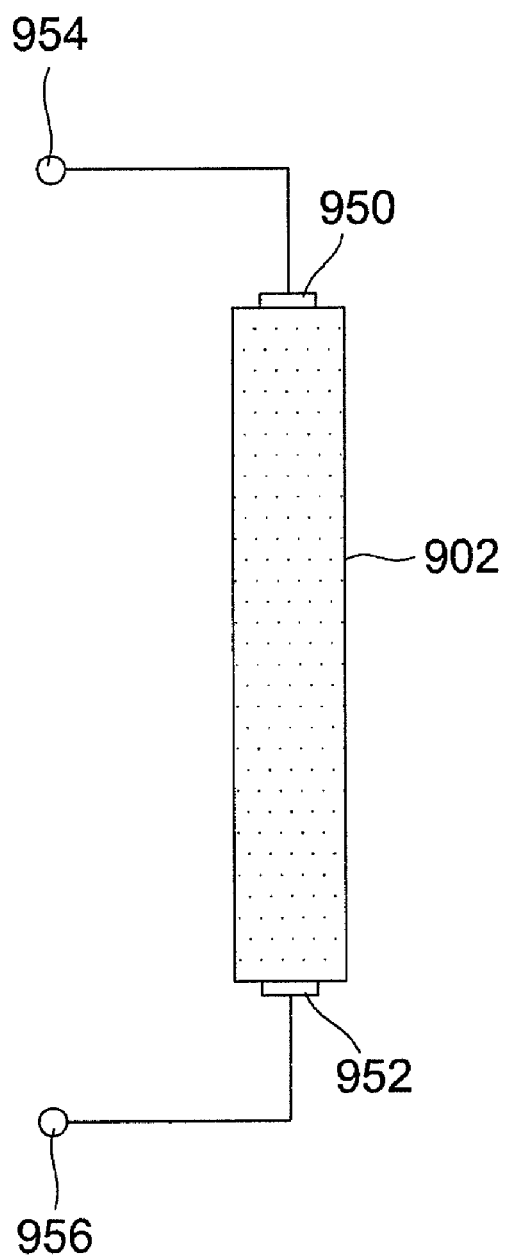
FIG. 12 illustrates an exemplary resistance device that uses the hydrated substrate of FIG. 9.
Figure 13:
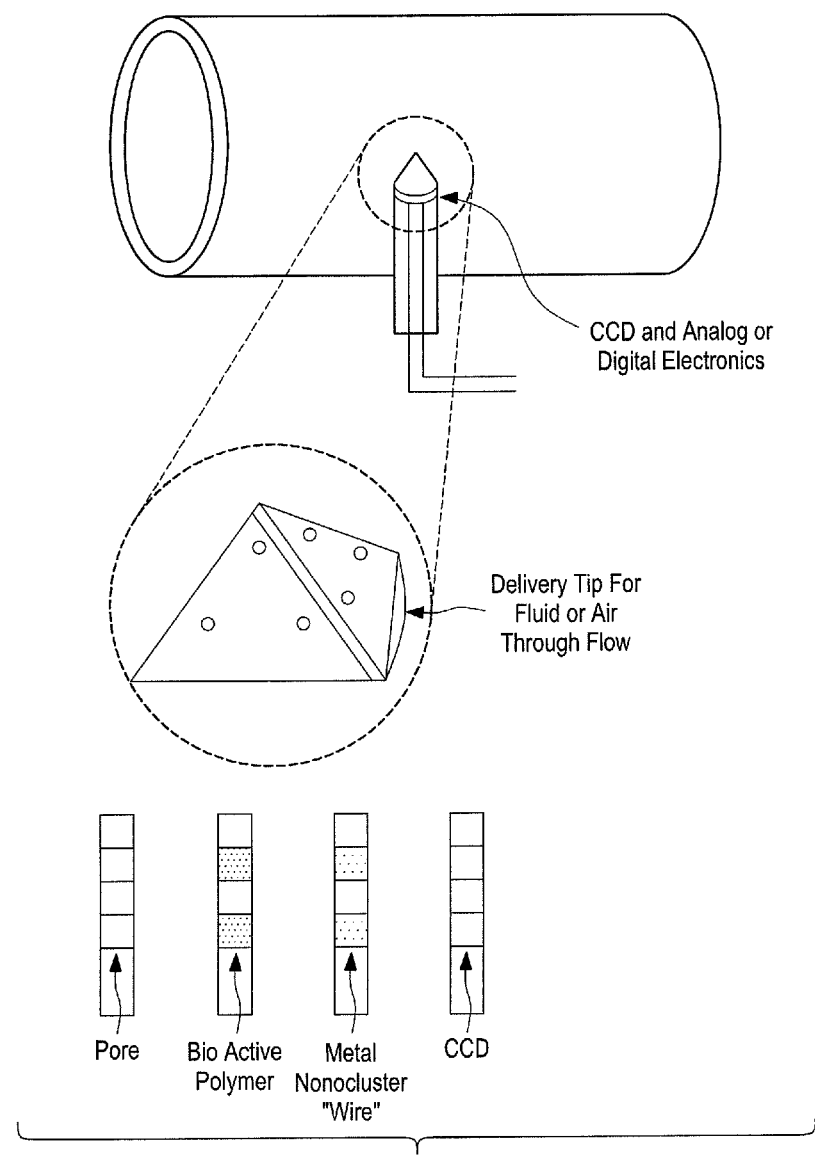
FIG. 13 illustrates an exemplary detection probe that utilizes the materials provided by the processing method of FIG. 7.
Figure 14:
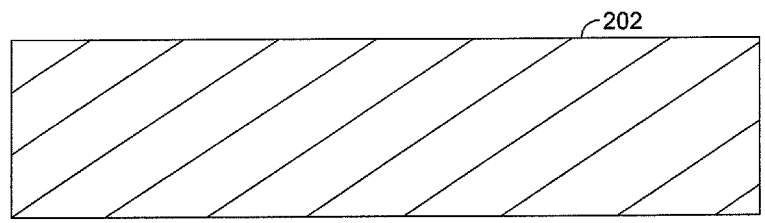
FIG. 14 depicts a cross-sectional view of an exemplary hydrated substrate.

The presence of target material may also be detected by observing changes in electrical properties. By placing metal strips 940, 942, serving as electrodes as shown in FIG. 11, on the edges of the strips of detection material, variations in capacitance, due to changes in the dielectric constant, may be observed by an electrical measurement circuit connected to terminals 944, 946 thereby indicating the presence of a target material. A similar arrangement as shown in FIG. 12 may be used to observe changes in conductivity for determining the presence of target materials. Electrodes 950, 952 are placed on the ends of the strips 962, and terminals 954, 956 are available for making resistance measurements.

It should be further emphasized that the above-described embodiments of the present invention, particularly, any "preferred" embodiments, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

Now, therefore, the following is claimed:

1. A sensor for detecting the presence of a target material in a medium, the sensor comprising:
    a hydrated substrate comprising a liquid crystal polymer, wherein the hydrated substrate has molecular spaces formed between polymeric chains of the hydrated substrate, and wherein the hydrated substrate has water molecules entrapped within the molecular spaces;
    detection material attached to the hydrated substrate, wherein the detection material has a specific affinity for the target material, wherein a detectable change in charge occurs when the target material and the detection material coalesce, and wherein the water molecules entrapped within the molecular spaces provide a water source for the detection material thereby enabling the detectable change in charge when the target material is present; and
    a display coupled to a detection plate on a surface of the hydrated substrate, wherein the display indicates the presence of target material in response to the change in charge.

2. The sensor of claim 1, wherein additional detection materials are bonded to the hydrated substrate for detecting additional target materials.

3. The sensor of claim 2, wherein the detection material and the additional detection materials are deposited as parallel areas.

4. The sensor of claim 1, wherein the detection material is bonded to a top surface of the hydrated substrate.

5. The sensor of claim 4, wherein the display is coupled to the detection plate on a bottom surface of the hydrated substrate.

6. A method for detecting a target material by generating a detectable change of charge, the method comprising the steps of:
    bonding detection material to a hydrated substrate comprising a liquid crystal polymer (LCP), wherein the detection material has a specific affinity for the target material and wherein a change in charge occurs when the target material and the detection material coalesce, the hydrated substrate having molecular spaces formed between polymeric chains of the hydrated substrate, wherein water molecules reside within the molecular spaces;
    attaching a charge detector to the hydrated substrate for detecting the change in charge;
    placing the hydrated substrate in a medium suspected of having the target material;
    detecting the change in charge; and
    indicating when the target material is present in response to the detecting step.

7. The method of claim 6, wherein the indicating step comprises the step of displaying an indication on a display unit.

8. The method of claim 7, wherein the bonding step comprises the step of bonding the detection material to a top surface of the hydrated substrate, and wherein the attaching step comprises the step of attaching the charge detector to a bottom surface of the hydrated substrate.

9. The method of claim 6, further comprising the steps of:
    heating the LCP;
    introducing bubbles into the heated LCP thereby forming the molecular spaces between the polymeric chains; and
    migrating the water molecules into the molecular spaces.

10. The method of claim 9, further comprising the step of controlling sizes of the bubbles such that the water molecules become entrapped within the molecular spaces.

11. The method of claim 9, further comprising the step of dispersing metal ions between cross links of the polymer chains.

12. A system for determining the presence of a target material within a medium, the system comprising;
    a hydrated substrate comprising a liquid crystal polymer, wherein the hydrated substrate has detection material that has a specific binding affinity for the target material, and wherein the hydrated substrate has water molecules entrapped within molecular spaces formed between polymeric chains of the hydrated substrate;
    a charge detection element attached to the hydrated substrate, wherein the charge detection element detects changes in charge when the target material and detection material coalesce, and wherein the water molecules entrapped within the molecular spaces provide a water source for the detection material thereby enabling the detectable change in charge when the target material is present;
    a processing unit for processing the output of the detection element and providing a signal for a display unit; and
    a display unit for receiving the signal from the processing unit and displaying information about the target material.

13. A method, comprising the steps of:
    providing a hydrated substrate comprising a liquid crystal polymer (LCP), the hydrated substrate having detection material and water molecules, the water molecules entrapped within molecular spaces formed between polymeric chains of the hydrated substrate, the detection material having a specific affinity for a target material;
    sensing a change in the detection material; and indicating a presence of the target material in response to the sensing step.

14. The method of claim 13, further comprising the steps of:
heating the LCP;
introducing bubbles into the heated LCP thereby forming the molecular spaces between the polymeric chains; and
migrating the water molecules into the molecular spaces.

15. The method of claim 14, further comprising the step of controlling sizes of the bubbles such that the water molecules become entrapped within the molecular spaces.

16. The method of claim 14, further comprising the step of dispersing metal ions between cross links of the polymer chains.

* * * * *